United States Patent
DeLuca et al.

(10) Patent No.: US 10,772,551 B2
(45) Date of Patent: Sep. 15, 2020

(54) COGNITIVE PROGRESS INDICATOR

(71) Applicant: International Business Machines Corporation, Armonk, NY (US)

(72) Inventors: Lisa Seacat DeLuca, San Francisco, CA (US); Clifford A. Pickover, Westchester, NY (US); Dana L. Price, Surf City, NC (US); Aaron J. Quirk, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 303 days.

(21) Appl. No.: 15/590,675

(22) Filed: May 9, 2017

(65) Prior Publication Data
US 2018/0325441 A1 Nov. 15, 2018

(51) Int. Cl.
*A61B 5/16* (2006.01)
*G06F 11/32* (2006.01)

(52) U.S. Cl.
CPC ............ *A61B 5/165* (2013.01); *G06F 11/328* (2013.01)

(58) Field of Classification Search
None
See application file for complete search history.

(56) References Cited

U.S. PATENT DOCUMENTS

| | | | |
|---|---|---|---|
| 5,644,334 A | 7/1997 | Jones et al. | |
| 6,290,504 B1 | 9/2001 | Benitz et al. | |
| 7,665,024 B1* | 2/2010 | Kondziela | G06F 3/011 715/745 |
| 7,930,676 B1* | 4/2011 | Thomas | G06F 9/44505 706/45 |
| 8,430,299 B2 | 4/2013 | Poslinski et al. | |
| 8,621,416 B1* | 12/2013 | Thomas | G06F 9/44505 706/45 |
| 8,666,818 B2 | 3/2014 | DeVree | |
| 8,737,800 B2 | 5/2014 | Schmehl | |
| 8,869,115 B2* | 10/2014 | Bruns | G06F 9/451 717/124 |
| 9,547,408 B2* | 1/2017 | Bromer | G06F 3/011 |
| 10,187,254 B2* | 1/2019 | Li | G06Q 30/02 |
| 10,235,466 B2* | 3/2019 | Brunn | G06F 16/9535 |
| 2001/0055017 A1* | 12/2001 | Ording | G06F 3/0481 345/440 |
| 2003/0046401 A1* | 3/2003 | Abbott | G06F 9/451 709/228 |
| 2004/0190607 A1* | 9/2004 | Wakimoto | H04N 5/76 375/240.01 |

(Continued)

OTHER PUBLICATIONS

Galindo; "Toward a UI Adaptation Approach Drive by User Emotion"; Mar. 2017; http://iihm.imag.fr/publs/2017/GalindoACHI2017.pdf (Year: 2017).*

(Continued)

*Primary Examiner* — Eddy Saint-Vil
*Assistant Examiner* — William D Ermlick
(74) *Attorney, Agent, or Firm* — Scully, Scott, Murphy & Presser, P.C.; Kevin M. Jordan, Esq.

(57) ABSTRACT

A status indicator provides a graphical representation of progress of a task to a user. A cognitive state of the user is detected by a computer operatively coupled to one or more sensors or cameras. The progress indicator is automatically modified by the computer in response to detecting the cognitive state of the user.

17 Claims, 6 Drawing Sheets

(56) References Cited

U.S. PATENT DOCUMENTS

| | | | |
|---|---|---|---|
| 2006/0190822 A1* | 8/2006 | Basson | G06Q 10/10 715/700 |
| 2006/0277467 A1* | 12/2006 | Reponen | G06F 3/011 715/708 |
| 2007/0088833 A1* | 4/2007 | Yang | G06F 16/41 709/227 |
| 2007/0094267 A1* | 4/2007 | Good | G06F 16/954 |
| 2007/0294273 A1* | 12/2007 | Bendeck | G06F 16/68 |
| 2008/0256474 A1* | 10/2008 | Chakra | G06F 3/0481 715/772 |
| 2009/0070699 A1 | 3/2009 | Birkill et al. | |
| 2009/0083781 A1 | 3/2009 | Yang et al. | |
| 2009/0113334 A1* | 4/2009 | Chakra | G06F 9/4443 715/772 |
| 2010/0082516 A1* | 4/2010 | Basu | G05B 13/048 706/47 |
| 2011/0166777 A1* | 7/2011 | Chavakula | G01C 21/3667 701/533 |
| 2011/0283189 A1* | 11/2011 | McCarty | H04N 5/44543 715/707 |
| 2012/0226993 A1* | 9/2012 | Bromer | G06F 3/011 715/744 |
| 2012/0319869 A1* | 12/2012 | Dorfmann | A61B 5/18 340/945 |
| 2013/0212514 A1* | 8/2013 | Li | G06F 3/0484 715/772 |
| 2013/0219013 A1* | 8/2013 | Decker | H04L 67/02 709/217 |
| 2013/0235044 A1* | 9/2013 | Kaleta | G06F 3/0484 345/473 |
| 2013/0239039 A1* | 9/2013 | Kaleta | G06F 3/0484 715/772 |
| 2013/0239040 A1 | 9/2013 | Kaleta et al. | |
| 2013/0246962 A1* | 9/2013 | Kaleta | G06F 3/0484 715/772 |
| 2014/0229830 A1 | 8/2014 | Schmehl | |
| 2014/0316867 A1* | 10/2014 | Rosen | G06F 3/04812 705/14.6 |
| 2015/0012225 A1* | 1/2015 | Mattila | G16H 50/30 702/19 |
| 2015/0098691 A1* | 4/2015 | Avrahami | G11B 27/3036 386/241 |
| 2015/0119198 A1* | 4/2015 | Wisbey | A61B 5/02405 482/9 |
| 2015/0318020 A1 | 11/2015 | Pribula | |
| 2016/0050169 A1* | 2/2016 | Ben Atar | H04M 1/72544 709/206 |
| 2016/0077675 A1* | 3/2016 | Rav-Acha | G06T 1/0007 715/703 |
| 2016/0349937 A1* | 12/2016 | Harrison | G06F 17/2247 |
| 2016/0358491 A1* | 12/2016 | Young | G09B 5/00 |
| 2016/0378286 A1* | 12/2016 | Ke | G06F 3/017 715/764 |
| 2016/0378965 A1* | 12/2016 | Choe | G06F 21/32 726/19 |
| 2017/0000348 A1* | 1/2017 | Karsten | G06F 19/3418 |
| 2017/0004459 A1* | 1/2017 | Karsten | G06F 19/3418 |
| 2017/0031559 A1* | 2/2017 | Lee | G06F 3/0488 |
| 2017/0041272 A1* | 2/2017 | Chang | H04L 51/063 |
| 2017/0168703 A1* | 6/2017 | Feris | G06F 3/04855 |
| 2017/0289619 A1* | 10/2017 | Xu | H04N 21/251 |
| 2017/0316707 A1* | 11/2017 | Lawrenson | G09B 5/04 |
| 2018/0130373 A1* | 5/2018 | Bernard-Paroly | G09B 19/0038 |
| 2018/0240027 A1* | 8/2018 | Karanam | G16H 50/30 |
| 2018/0302687 A1* | 10/2018 | Bhattacharjee | H04N 21/4884 |
| 2019/0014378 A1* | 1/2019 | Shah | H04N 21/44218 |
| 2019/0015751 A1* | 1/2019 | Kahn, II | A63F 13/67 |

OTHER PUBLICATIONS

Martin; "Designing Responsive Interactive Applications by Emotion-Tracking and Pattern-Based Dynamic User Interface Adaptation"; Jul. 2016; International Conference on Human-Computer Interaction (Year: 2016).*

Xiangyang, Li. et al., "Active Affective State Detection and User Assistance With Dynamic Bayesian Networks", IEEE Transactions on Systems, Man, and Cybernetics—Part A: A System and Humans, vol. 35, No. 1, Jan. 2005, pp. 93-105.

Osman, A. et al., "Evaluating the Effects of Animation on Mobile Application Learnability", 2010 Second International Conference on Computer Engineering and Applications, 2010, pp. 509-512.

Hurter, C., "Active Progress Bar: Aiding the switch to temporary activities", Proceedings of the BCS HCI 2012 People and computers XXVI, 2012 pp. 99-108.

Gaved, M., et al. "MASELTOV Deliverable Report 7.2: Feedback and Progress Indicators", 2013, pp. 1-50.

* cited by examiner

US 10,772,551 B2

COGNITIVE PROGRESS INDICATOR

FIELD

The present invention relates generally to graphical user interfaces and, more particularly, to an interface that indicates a cognitive state of a user.

BACKGROUND

A graphical user interface component (sometimes referred to as a progress bar, or status bar) and individually or collectively referred to herein as an indicator and/or a progress/status indicator can be used to convey a status of a task, operation, or process (a "task"). By way of example only, a progress/status indicator may be provided in the form of a slider bar that moves from a starting position towards an ending position and the task may include a loading of a web page, a file download, a download or installation of a computer application, or a transfer of data. The position of the progress/status indicator may be updated dynamically as the completion status of the task changes and/or the indicator may explicitly convey the status as a percentage of the task being completed. In some cases, where a progress/status indicator is not indicative of a percentage completion of the task, an indeterminate-type indicator may display a discrete amount of a task completed, such as a number of pages printed so far.

SUMMARY

The following summary is merely intended to be exemplary. The summary is not intended to limit the scope of the claims.

A computer-implemented method embodiment of the present invention comprises providing a graphical representation of a status indicator, wherein the status indicator is indicative of a progression of a task from a commencement of the task to a completion of the task while the task is being performed. A cognitive state is detected by the computer, and the status indicator is modified by the computer in response to said detecting the cognitive state.

Other embodiments include a computer program product and a system.

BRIEF DESCRIPTION OF THE SEVERAL VIEWS OF THE DRAWINGS

The foregoing aspects and other features are explained in the following description, taken in connection with the accompanying drawings, wherein.

DETAILED DESCRIPTION

Figure 1:
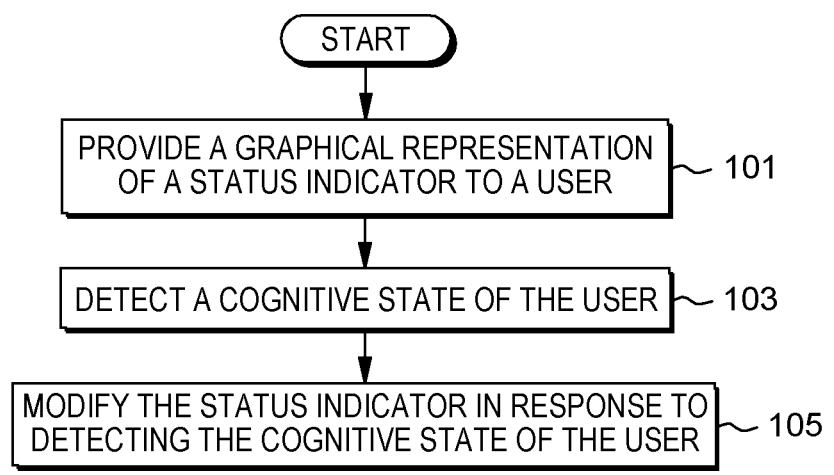
FIG. 1 illustrates an exemplary computer-executed method in accordance with one or more embodiments of the invention.

FIG. 1 illustrates an exemplary computer-implemented method in accordance with one or more embodiments of the invention. The method commences at block 101 where a graphical representation of a status indicator, such as a progress indicator or progress bar, is displayed to a user. The status indicator is indicative of a graduated progression of a task from a commencement of the task to a completion of the task while the task is being performed. A cognitive state of the user is detected at block 103. This step is performed using one or more sensors, or one or more cameras, or any of various combinations thereof, that are operatively coupled to a computer. For purposes of illustration only, the cognitive state may include an emotional or psychological state comprising any of fatigue, frustration, anger, distraction, impatience, happiness, sadness, or surprise. Alternatively or additionally, the cognitive state may be related to a user type or user cohort. Some examples of user types and user cohorts include autistic individuals, children, the elderly, individuals suffering from mild cognitive impairments due to neurodegenerative diseases, pre-Alzheimer's individuals, individuals having a cognitive disability, or individuals having attention-deficit disorder ("ADD"). Alternatively or additionally, the cognitive state may relate to one or more cognitive styles. These cognitive styles may occur, for example, with respect to a population of normal individuals.

A cognitive style describes the way an individual thinks, perceives and remembers information. A cognitive style differs from cognitive ability (or level), the latter being measured by aptitude tests or so-called intelligence tests. For purposes of illustration, one popular test for measuring cognitive style is called the Myers-Brigg Type Indicator ("MBTI"). MTBI is an introspective, self-reporting questionnaire designed to indicate and reveal psychological preferences in how people perceive the world and make decisions. It is based on a typological theory proposed by Carl Jung who had speculated that there are four principal psychological functions by which humans experience the world—sensation, intuition, feeling, and thinking—and that one of these four functions is dominant for a given individual most of the time. The MBTI was constructed for normal populations and emphasizes the value of naturally-occurring differences. The underlying assumption of the MBTI is that every individual has specific preferences in the way that they construe their experiences, and these preferences underlie an individual's interests, needs, values, and motivation.

Another exemplary test for measuring cognitive style is called Cognitive Style Analysis ("CSA"). CSA is a two-dimensional computer-implemented test that measures individuals' positions along a first dimensional axis and a second dimensional axis orthogonal to the first dimensional axis. The first dimensional axis represents a Wholist-Analytic (W-A) scale. The second dimensional axis represents a Verbal-Imagery (V-I) scale. The W-A scale reflects how individuals organize and structure information. Individuals described as Analytics will deconstruct information into its component parts, whereas individuals described as Wholists will retain a global or overall view of information. The V-I dimension describes individuals' modes of information representation in memory during thinking. Verbalizers represent information in words or verbal associations, and Imagers represent information in mental pictures.

Figure 7:
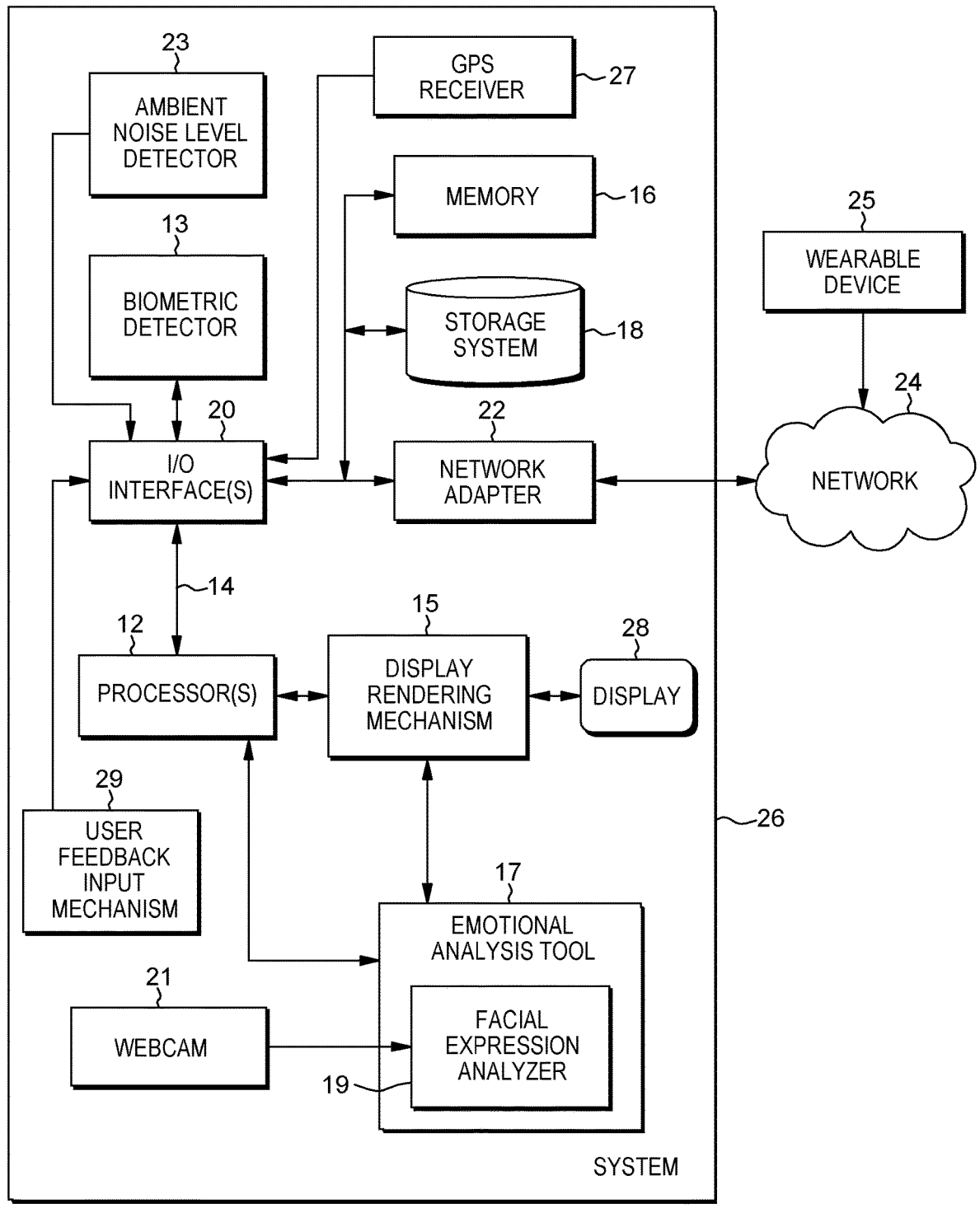
FIG. 7 illustrates an exemplary system in accordance with one or more embodiments of the present invention.

With reference again to block 103 and by way of preview to FIG. 7, the cognitive state of the user may be detected using a system 26 (FIG. 7) that includes one or more sensing mechanisms, or one or more cameras, or any of various combinations thereof. For example, the system 26 may include a computer-implemented emotional analysis tool 17, a biometric detector 13, and an ambient noise level detector. By way of further preview and example only, one or more such systems can be associated along with one or more additional devices, such as a wearable device, smartphone, or laptop computer that are being used concurrently. Some examples of the system 26 embodying such tools, detection components and devices will be discussed in more detail with reference to FIG. 7.

In some embodiments, the detection of cognitive state can include a determination of a level of possible distraction, based, for example, on a number or quantity of open applications or activities (windows) on one or more systems and/or devices. The detection may also include a determination of a level of fatigue based on: an assessment of a daily meeting schedule or electronic calendar, an input from a wearable device, a context determined from the user's present geographic location (for example, using a global positioning system ("GPS") receiver), the time of day, day of the week, or any of various combinations thereof.

Alternatively or additionally, the detection of the cognitive state at block 103 (FIG. 1) may consider caregiver input, a user profile, a user demographic, or any of various combinations thereof. For example, optionally, a user profile may specify a range of conditions, styles, and tendencies for certain states, and these specified parameters may be supplied by a user, family member, or caregiver. For instance, one may consider a conditions and features in a table, having labels such as: "mild cognitive impairment, autism, visually impaired, impatient style." Other labels may be used in addition to, or in lieu of, the foregoing labels. Each of these parameters or table entries may also be associated with a value, such as low, medium, or high.

In some cases, a user profile is not needed because the system 26 (FIG. 7) (to be discussed in greater detail hereinafter) may infer or automatically learn such features based upon a monitoring of user behavior over time. For example, an impatient style may be assigned to an individual who often gives up during an installation of a software program that takes 3 minutes to reach a 70% level as displayed on a tiny, plain, boring-looking progress bar. A real-time estimate of distraction level may be inferred by noting that a user is shifting attention between 5 different open windows on a computer desktop while a phone is ringing and an instant message for the user has popped up. In some embodiments, one or more conditions or features may be provided in an opt-in manner, if a user chooses to supply such information or to be monitored. Such information may be encrypted to help ensure privacy.

Referring again to FIG. 1, the process advances from block 103 to block 105 where the status indicator (such as a progress bar display) is modified by the computer in response to the detected cognitive state of the user. By way of example only, such a modification may be performed by a display rendering mechanism in conjunction with the emotional analysis tool 17 (FIG. 7) (examples of which will be discussed in greater detail hereinafter with reference to FIG. 7). The status indicator may comprise a progress bar that is displayed by itself, or displayed in conjunction with one or more additional graphical elements.

The status indicator may be modified by changing one or more of a color of the status indicator, a color of one or more additional graphical elements or shapes that are displayed in conjunction with the status indicator, a size of the status indicator, a size of one or more additional graphical elements or shapes that are displayed in conjunction with the status indicator, a shape of the status indicator, a movement or rotation of the status indicator, a movement or rotation of the one or more additional graphical elements or shapes that are displayed in conjunction with the status indicator, a change in a speed of rotation of the rotating shape, a position of the status indicator, a position of one or more additional graphical elements that are displayed in conjunction with the status indicator, a style of the status indicator, a rotating pinwheel associated with the status indictor, or a style of one or more additional graphical elements that are displayed in conjunction with the status indicator.

Alternatively or additionally, the status indicator may be modified by providing a textual description or textual element associated with the status indicator, or by changing the textual description or textual element. For example, the textual element may be selected so as to soothe or entertain a user. Alternatively or additionally, the status indicator may be modified by changing one or more graphical attributes of the progress bar, or by performing a mathematical transformation of a level of progress indicated by the progress bar such as a logarithmic indication of actual progress or a first derivative of actual progress. Alternatively or additionally, the status indicator may be modified by providing a moving shape such as a spinning pinwheel, or by displaying a graphical, virtual, or pictorial scene intended to soothe or entertain a user.

Alternatively or additionally, playback of a music file, a sound file, a video file, or a streaming media file may be initiated in response to the detected cognitive state of the user. The music file may represent, for example, the user's favorite song. The sound file may include, for example, a joke or an amusing saying. Alternatively or additionally, a portion of a music, sound, or video file currently being downloaded may be played back. Alternatively or additionally, the status indicator may be provided in the form of a graphical depiction of a structure such as a totem pole, building, or pyramid, where the height or size, or both, of the structure is adjusted in accordance with the level of progress to thereby provide a graphical status indicator. Alternatively or additionally, the status indicator may include a puzzle or riddle to be solved by the user.

Status indicators have an interesting cognitive component. When the user observes that some progress is being made with a task, operation, or process, the user can be coaxed into feeling better about an undesirably slow progress. Moreover, when a user is uncertain that a given operation is still in progress, the user may falsely assume that their computing device is hanging, or that the computing device is waiting for further user input. Time may be wasted if the user reboots their computing device based upon an erroneous belief that the device is hanging when, in reality, the device is in the middle of a lengthy, time-consuming process. Using the status indicator to reassure the user that an operation is in progress and that something is happening may prevent the user from unnecessarily rebooting their computing device.

Figure 2:
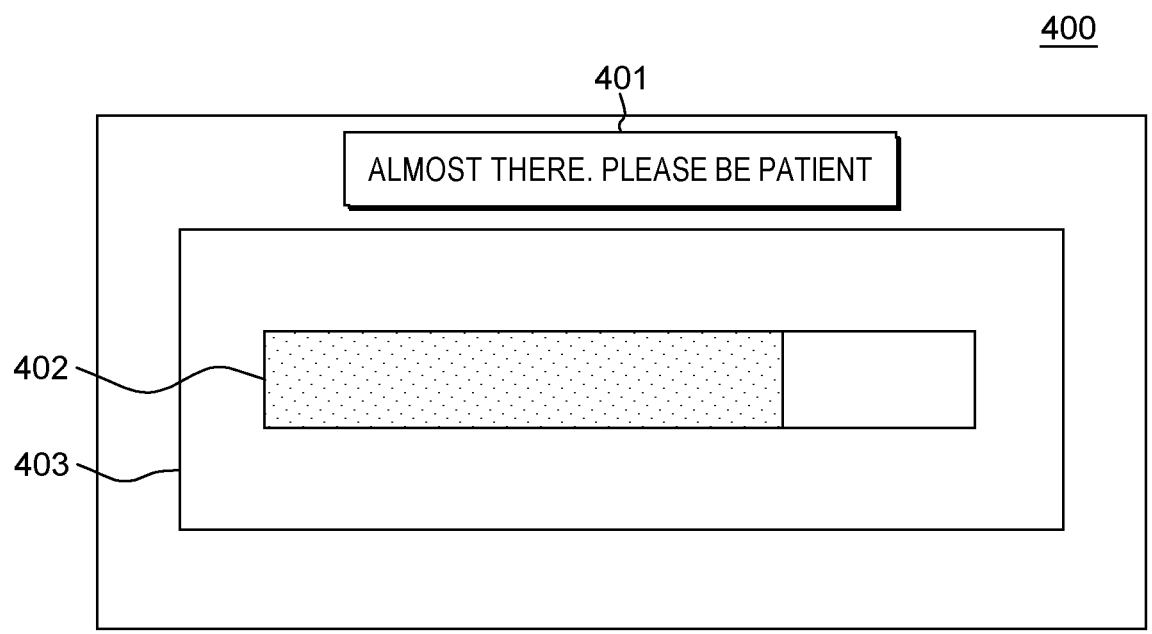
FIG. 2 shows a first example of a status indicator generated in accordance with one or more embodiments of the invention.

FIG. 2 shows a first example of a status indicator 400 generated in accordance with one or more embodiments of the invention. The status indicator 400 is indicative of a progression of a task from a commencement of the task to a completion of the task while the task is being performed. The status indicator 400 includes a textual element 401, a progress bar 402, and a progress bar background 403. The textual element states, "Almost there. Please be patient." This textual element 401 may be displayed, for example, in response to the detected cognitive state of the user being impatience or distraction. On the other hand, if the detected cognitive state of the user was sadness, the textual element 401 may display a different message such as "Don't worry, be happy! Your download is almost complete." Alternatively or additionally, the progress bar background 403 may be changed from a first color to a second color in response to the detected cognitive state of the user being impatience or distraction. Likewise, the progress bar background 403 may be changed from the first color to a third color in response to the detected cognitive state of the user being sadness.

Figure 3:
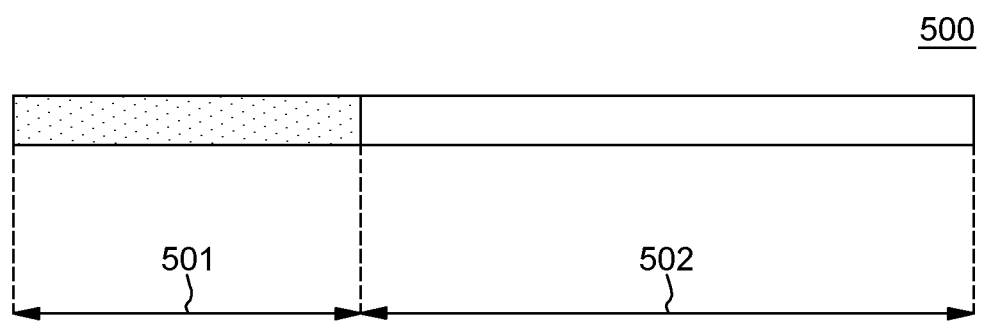
FIG. 3 shows a second example of a status indicator generated in accordance with one or more embodiments of the invention.

FIG. 3 shows a second example of a status indicator 500 generated in accordance with one or more embodiments of the invention. The status indicator 500 is indicative of a progression of a task from a commencement of the task to a completion of the task while the task is being performed. The status indicator 500 includes a first portion 501 and a second portion 502. The first portion 501 and the second portion 502 together indicate a total duration of a recorded or downloaded media content. The first portion 501 indicates a portion or section of the recorded or downloaded media content that has already been viewed or played back. For example, the first portion 501 may be shown using a first color such as red (not depicted), and the second portion 502 may be shown using a second color such as green (not depicted). Alternatively or additionally, the first color or the second color, or both, may be selected or specified by the user. The status indicator 500 (FIG. 3) is modified at block 105 (FIG. 1) in response to detecting the cognitive state of the user at block 103 (FIG. 1). For example, if the cognitive state of the user is anger, anxiety, or nervousness, the colors of the first portion 501 (FIG. 3) and the second portion 502 may be changed to gentle, soothing pastel colors, such as light blue or pink for the first portion 501, and pale yellow for the second portion 502. On the other hand, if the cognitive state of the user is fatigue or tiredness, the colors of the first portion 501 and the second portion 502 may be changed to bright, invigorating colors, such as bright orange for the first portion 501, and deep purple of bright violet for the second portion 502.

Figure 4:
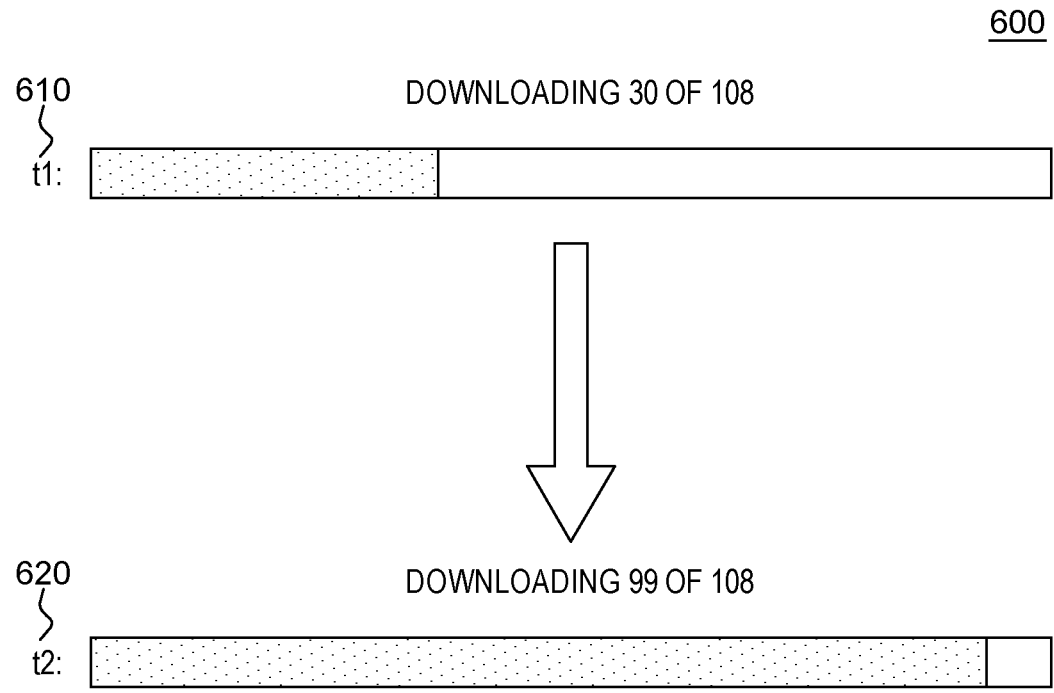
FIG. 4 shows a third example of a status indicator generated in accordance with one or more embodiments of the invention.

FIG. 4 shows a third example of a status indicator 600 generated in accordance with one or more embodiments of the invention. The status indicator 600 is indicative of a progression of a task from a commencement of the task to a completion of the task while the task is being performed. At a first time t1 610, the status indicator 600 has a first size. At a second time t2 620 subsequent to the first time t1, the status indicator 600 has expanded to a second size greater than the first size. For example, at the time t1 610, a file download is in its initial stages, with 30 of 108 megabytes having been downloaded. At this time, the status indicator 600 is relatively small. Then, at time t2 620 when substantial progress has been made in downloading the file, with 99 of 108 megabytes being downloaded, the status indicator 600 has expanded to a much larger size than at time t1 601. The expansion of the status indicator 600 from time t1 601 to time t2 602 may occur according to a linear function, a logarithmic function, or a stepwise function, for example. The status indicator 600 (FIG. 4) can be modified at block 105 (FIG. 1) in response to detecting the cognitive state of the user at block 103 (FIG. 1). For example, if the cognitive state of the user is irritation or impatience, the size of the status indicator 600 is decreased if progress is less than 50% of completion, but if progress is greater than 50% of completion, the size of the status indicator 600 is increased. If the cognitive state of the user is distraction or fatigue, the status indicator 600 may be configured to rapidly flash on and off, or to rapidly flash between a first set of colors and a second set of colors.

The status indicator 600 of FIG. 4 may be employed, for example, in situations where the cognitive state of the user is such that the user is on edge, having a rough day, heavily distracted, or impatient. Such a user is annoyed when constantly reminded that the Internet connection is slow and it seems to be taking forever to download some software or media content. Thus, the status indicator 600 is first displayed in a very small size when the download first commences. Once the task gets close to completion, the status indicator 600 is displayed in a much larger size to emphasize that the progress of the download is almost finished.

Figure 5:
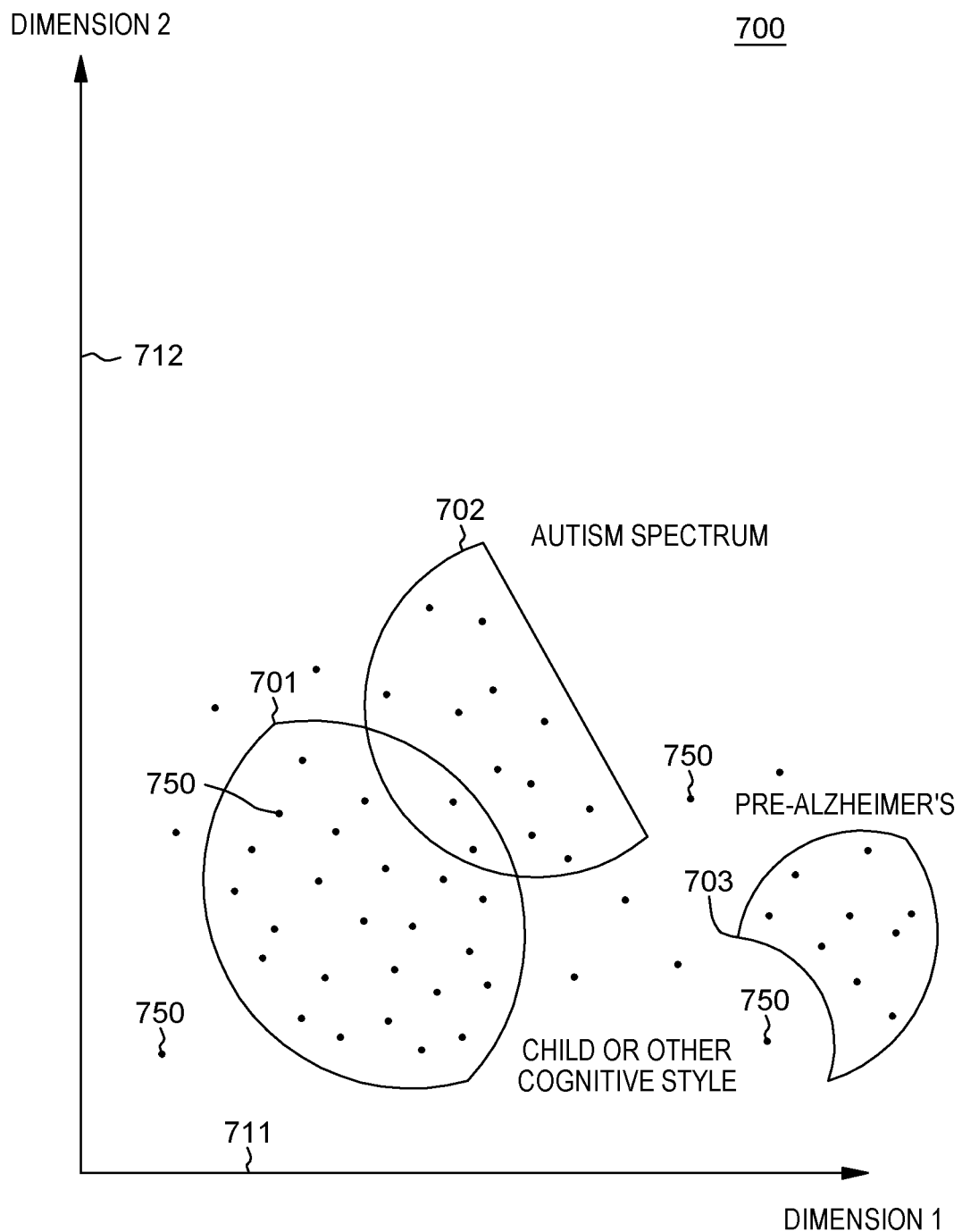
FIG. 5 is a graph illustrating a plurality of user classes for modifying or customizing status indicators, in accordance with one or more embodiments of the invention.

FIG. 5 is a graphical example of a plurality of cohorts (classes of user) for modifying or customizing progress bar displays. By way of example only, a representation of the status indicator 400 (FIG. 2), 500 (FIG. 3) or 600 (FIG. 4) may be changed or modified based on detection of a cognitive state of a user, and/or an associated user cohort. By way of further example only, a first cohort 701 (FIG. 5) may include one or more cognitive styles which are commonly used by children. A second cohort 702 can include autistic individuals, and a third cohort 703 can include pre-Alzheimer's individuals. A dimension one 711 can correspond to a first feature of the progress bar display 400 (FIG. 2), 500 (FIG. 3) or 600 (FIG. 4), and a dimension two 712 (FIG. 5) can correspond to a second feature of the progress bar display. Each of the dots 750 depicted in the graph 700 can represent an individual of the applicable cohort. For each of the plurality of respective cohorts 701, 702, 703, or classes of users, a corresponding progress bar representation may be selected that is designed or customized to meet one or more special needs or requirements of a specific user class of the plurality of respective user classes. For example only: Lisa may work better with a progress bar that shows linear progress; Andrzej may have attention deficit disorder ("ADD") and work better with a progress bar that flashes on and off; and Lori is autistic and works best with a progress bar that shows logarithmic progress.

Figure 6:
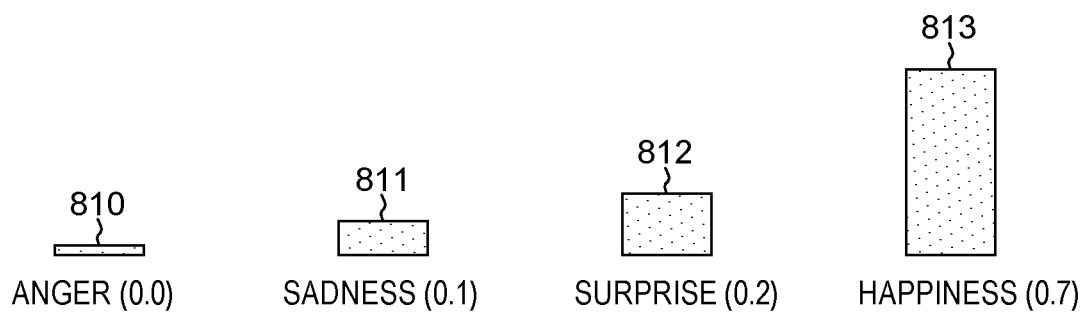
FIG. 6 shows an exemplary image of a user to be analyzed by image analysis software to determine a cognitive state of a user, in accordance with one or more embodiments of the present invention.
Figure 6:
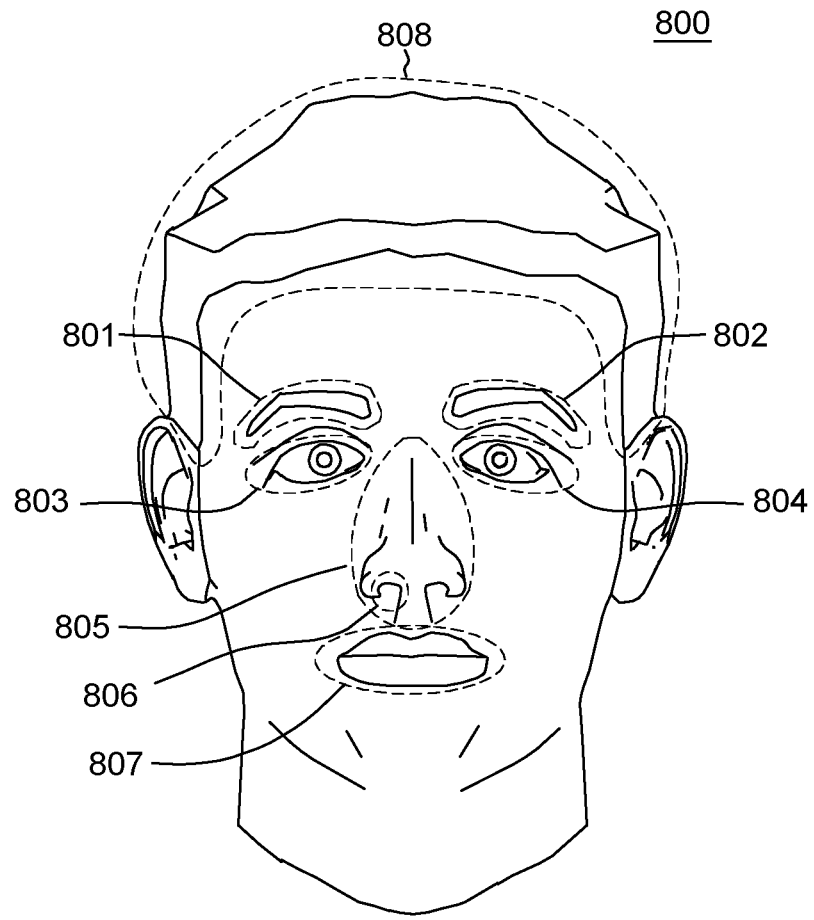

FIG. 6 shows an exemplary image to detect/determine a cognitive state of a user in accordance with the present invention. As depicted, an image 800 shows a user with a plurality of facial landmarks each associated with a set of segmented lines or curves, such as a first segmented curve 801, a second segmented curve 802, a third segmented curve 803, a fourth segmented curve 804, a fifth segmented curve 805, a sixth segmented curve 806, a seventh segmented curve 807, and an eighth segmented curve 808. For example, segmented curve 807 can track the corners of the user's mouth and can be used to determine whether the corners curve up or down. Segmented curves 801 and 802 can track the user's eyebrows as they raise and fall, for example.

FIG. 7 illustrates an exemplary system 26 in accordance with one or more embodiments of the present invention. It is understood that the system 26 depicted in FIG. 7 is only one example of a suitable system and is not intended to suggest any limitation as to the scope of use or functionality of embodiments of the present invention. In contrast, the system 26 shown may be operational with numerous other general-purpose or special-purpose computing system environments or configurations. Examples of well-known computing systems, environments, and/or configurations that may be suitable for use with the processing system shown in FIG. 7 include, but are not limited to, personal computer systems, server computer systems, thin clients, thick clients, handheld or laptop devices, multiprocessor systems, microprocessor-based systems, neural networks, set top boxes, programmable consumer electronics, network PCs, minicomputer systems, mainframe computer systems, and distributed cloud computing environments that include any of the above systems or devices, and the like. Some embodiments of the system 26 may be described in the general context of computer system executable instructions, such as program modules, being executed by a computer system. Generally, program modules may include routines, programs, objects, components, logic, data structures, and so on that perform particular tasks or implement particular abstract data types. Some embodiments of the computer system 26 may be practiced in distributed cloud computing environments where tasks are performed by one or more remote processing devices, such as mobile and/or wearable devices 25 (FIG. 7), that are communicably linked through a network 24. In a distributed cloud computing environment, program modules may be located in one or more local and/or remote computer system storage media including memory storage devices.

As depicted in FIG. 7, the system 26 may include, but is not limited to, one or more processors or processing units 12, a memory 16, and a bus 14 that couples various system components including system memory 16 to processor 12. For example, processor(s) 12 may execute one or more program modules that perform the methods described herein. In some embodiments, one or more parts of the modules may be programmed into the integrated circuits of the processor 12, loaded from memory 16, storage device 18, or network 24 or combinations thereof. Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The system 26 may include a variety of computer system readable media. Such media may be any available media that is accessible by computer system, and it may include both volatile and non-volatile media, removable and non-removable media. By way of example only, memory 16 can include computer system readable media in the form of volatile memory, such as random access memory (RAM), and/or cache memory, or others. System 26 may further include other removable/non-removable, volatile/non-volatile computer system storage media. By way of further example only, storage system 18 can be provided for reading from and writing to a non-removable, non-volatile magnetic media (such as a "hard drive"). Although not shown, exemplary media may include a magnetic disk drive for reading from and writing to a removable, non-volatile magnetic disk (such as a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

The system 26 may also communicate with one or more external devices. Such communication can occur via Input/Output (I/O) interfaces 20 and/or network adaptor 22. A few (non-limiting) examples of external devices include locally-attached devices that can help a user to interact with the system, such as: display 28, a keyboard, a pointing device, etc. By way of further example only, such communication may include one or more devices (such as a network card, modem, etc.) that enable the system to communicate with one or more other computing devices, such as wearable device(s) 25, via network 24.

Furthermore, the system 26 can communicate with one or more networks 24, such as a local area network (LAN), a general wide area network (WAN), and/or a public network (such as the Internet) via network adapter 22. As depicted, network adapter 22 communicates with the other components of computer system via bus 14. It should be understood that (although not shown) other hardware and/or software components could be used in conjunction with the system. Examples include, but are not limited to: microcode, device drivers, redundant processing units, external disk drive arrays, RAID systems, tape drives, and data archival storage systems, etc.

The emotional analysis tool 17 is a program or application that use a webcam 21, a video camera, or a still-image camera gather image data depicting the user. Image analysis software is then applied to the gathered image or images of the user to determine an emotional or cognitive state for the user. One example of a computer-executed emotional analysis tool 17 is called Clmtrackr™, which was created by a Norwegian computer scientist named Audun Øygard. Clmtrackr™ is a program that analyzes facial expressions based on video or image input. The program is written in JavaScript™ and runs in any of a variety if Internet browsers—no software downloads are required. In order to use the Clmtrackr™ tool, the user turns on the webcam 21 and stares into the webcam 21 while remaining as motionless as possible.

The Clmrackr™ tool applies a facial expression analyzer 19 programmed to implement a tracking algorithm to the image or images gathered by the webcam 21, to generate an output representative of one or more emotions being experienced by the user. The facial tracking is accomplished through a technique known as the constrained local model, or CLM. CLM is a type of algorithm that draws on a multiplicity of existing pictures of faces (for example, thousands of faces) to identify facial features and predict how these features will look when the face is scrunched into a smile, for example, or drooping into a frown. Based upon prior training, the facial tracking algorithm learns how to interpret each of a plurality of facial landmarks. Then, when confronted with a new face, the facial tracking algorithm goes looking for those facial landmarks that it has learned to find.

The output of the emotional analysis tool 17 specifies which of one or more emotions are being experienced by the user. In the example of FIG. 6, the emotions include anger 810, sadness 811, surprise 812, and happiness 813. If a plurality of emotions are being experienced by the user, the output specifies a relative ratio or percentage for each of the plurality of emotions. For instance, anger 810 is present in a ratio or percentage of 0.0, sadness 811 is present in a ratio or percentage of 0.1, surprise 812 is present in a ratio or percentage of 0.2, and happiness 813 is present in a ratio or percentage of 0.7.

The technology underpinning Clmtrackr™ and other emotional analysis tools 17 (FIG. 7) can be used in conjunction with the procedure of FIG. 1 to help people with special needs or conditions such as autistic individuals, depressed individuals, individuals who are pre-Alzheimers, children, or the elderly. For example, doctors have found meaningful changes in facial expression as people recover from depression. When people are severely depressed, they tend to make many expressions of contempt or disgust that signal to other people, "stay away, leave me alone." As individuals recover from depression, they tend to exhibit more and more smiles, but ironically they also display more and more signs of sadness. The person who is feeling sadness wants more help from others. As someone is becoming less depressed, they might also appear to be more sad. These changes in facial expression can be used to infer the cognitive state of an individual, and to adjust or modify the progress bar in accordance with this inferred cognitive state.

Referring again to FIG. 7, feedback may be received by the system 26 through user feedback input mechanism 29, for example, in response to the user viewing the status indicator on display 28 (see also status indicator 400 (FIG. 2), 500 (FIG. 3) or 600 (FIG. 4). It should be understood that user feedback input is not limited to dynamically provided input, or to any specific user such as a primary user, and can include input from users such as (without limitation) caregivers.

In some embodiments, feedback can be used to adjust or alter a subsequent display of the status indicator 400 (FIG. 2), 500 (FIG. 3) or 600 (FIG. 4), thereby implementing an iterative learning process. By way of example only, user feedback can be provided to a progress bar display rendering mechanism 15 that can further use a machine learning algorithm (not depicted) component of emotional analysis tool 17 to learn what types of progress bars are most appropriate for each of a plurality of different cohorts (classes of user) so that other users can benefit from this learning.

In some embodiments, a user may provide feedback by tapping on a certain style of progress bar display on the display 28 when the user likes or prefers this style of display. In other embodiments, the progress bar display rendering mechanism 15 may receive input from the emotional analysis tool 17 indicating (with a certain minimum level of confidence) that the user is becoming impatient or nervous, or experiencing another change of emotional state. In this case, the progress bar display rendering mechanism 15 adjusts the status indicator 400 (FIG. 2), 500 (FIG. 3) or 600 (FIG. 4) in accordance with the change of emotional state as determined by the emotional analysis tool 17.

In some embodiments, the system 26 of FIG. 7 may learn what progress bars are useful for different scenarios or cohorts of users, so that one or more subsequent users can benefit as the system learns over time. For example, based on feedback provided, the emotional analysis tool 17 may detect that a particular cohort of users appreciates or does not appreciate a certain type of progress bar, and this information may not only benefit a present user but also other relevant users who may later utilize the system. In some embodiments, an iterative learning process is performed based on feedback from a present user, learning from the feedback to identify one or more progress bars that are useful for a specific user cohort corresponding to the present user, and applying the learning from the present user to a subsequent user in the specific user cohort to present the identified one or more progress bars to the subsequent user. The feedback may be received by the emotional analysis tool 17. For example, if a present user continually interrupts the progress of a downloaded software program or file, this might imply that the present user is not being benefitted from a certain style of progress bar, and thus the system 26 of FIG. 7 may attempt to learn to try another style of progress bar for such a user, and also for other subsequent users that are members of the same user cohort as the present user.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN)

or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method for representing a status indicator, the method comprising:
    providing, by the computer, a graphical representation of the status indicator on a user interface display, wherein the status indicator is indicative of a progression of a task from a commencement of the task to a completion of the task while the task is being performed;
    detecting, by the computer, a cognitive state of the user, said user cognitive state being inferred based on performing an assessment of entries in the user's electronic calendar that indicate a potential fatigue; and
    modifying, by the computer, the status indicator in response to said detecting the cognitive state, said modifying the status indicator comprising applying a mathematical transformation of a level of progress displayed by the status indicator, the mathematical transformation comprising a first derivative of the level of progress displayed by the status indicator or a logarithmic function of the level of progress displayed by the status indicator.

2. The computer-implemented method of claim 1 further comprising: using one or more sensors or cameras operatively coupled to the computer for detecting a further cognitive state comprising at least one of fatigue, frustration, anger, happiness, surprise, and a level of distraction.

3. The computer-implemented method of claim 1 wherein said detecting the cognitive state further comprises detecting a cognitive state of a user cohort, said user cohort selected from a group consisting of autism, a child, an elderly individual, an individual suffering from a cognitive impairment due to a neurodegenerative disease, or a cognitive style, said modifying being based on associating progress bars with different user cohorts.

4. The computer-implemented method of claim 1 wherein said detecting the cognitive state further comprises inferring the cognitive state based on information in at least one of a user profile, feedback received from a caregiver, and a user demographic.

5. The computer-implemented method of claim 1 wherein said modifying the status indicator in response to said detecting the cognitive state, further comprises: modifying one or more graphical attributes of the status indicator, a moving shape, a change in shape, a rotating shape, or a change in a speed of rotation of a rotating shape.

6. The computer-implemented method of claim 1 further comprising:
receiving feedback;
modifying the status indicator in response to said receiving feedback; and
iteratively learning and communicating said learning in response to said modifying.

7. The computer-implemented method of claim 6 wherein said iteratively learning and communicating said learning in response to said modifying, further comprises applying said learning from a present user to a subsequent user in a specific user cohort; and presenting a modified status indicator to the subsequent user.

8. A computer program product comprising a computer-readable storage medium having a computer-readable program stored therein, wherein the computer-readable program, when executed on a computer including at least one processor, causes the computer to:
provide a graphical representation of a status indicator on a user interface display, wherein the status indicator is indicative of a progression of a task from a commencement of the task to a completion of the task while the task is being performed;
detect a cognitive state of the user, said user cognitive state being inferred based on performing an assessment of entries in the user's electronic calendar that indicate a potential fatigue; and
modify the status indicator in response to said detecting the cognitive state, said modifying the status indicator comprising applying a mathematical transformation of a level of progress displayed by the status indicator, the mathematical transformation comprising a first derivative of the level of progress displayed by the status indicator or a logarithmic function of the level of progress displayed by the status indicator.

9. The computer program product of claim 8 wherein said computer is further caused to: use one or more sensors or cameras operatively coupled to the at least one processor for detecting a further cognitive state comprising at least one of fatigue, frustration, anger, happiness, surprise, and a level of distraction.

10. The computer program product of claim 8 wherein said detecting the cognitive state further comprises detecting a cognitive state of a user cohort, said user cohort selected from a group consisting of autism, a child, an elderly individual, an individual suffering from a cognitive impairment due to a neurodegenerative disease, or a cognitive style, wherein said computer-readable program causes the computer to modify based on associating progress bars with different user cohorts.

11. The computer program product of claim 8 wherein said detecting the cognitive state further comprises inferring the cognitive state based on information in at least one of a user profile, feedback received from a caregiver, and a user demographic.

12. The computer program product of claim 8 wherein said modifying the status indicator in response to said detecting the cognitive state, further comprises: modifying one or more graphical attributes of the status indicator, a moving shape, a change in shape, a rotating shape, or a change in a speed of rotation of a rotating shape.

13. The computer program product of claim 8 further configured for:
receiving feedback;
modifying the status indicator in response to said receiving feedback; and
iteratively learning and communicating said learning in response to said modifying.

14. The computer program product of claim 13 wherein said iteratively learning and communicating said learning in response to said modifying, further comprises applying said learning from a present user to a subsequent user in a specific user cohort; and presenting a modified status indicator to the subsequent user.

15. A system comprising at least one processor and a memory coupled to the at least one processor, wherein the memory comprises instructions which, when executed by the at least one processor, cause the at least one processor to:
provide a graphical representation of a status indicator on a user interface display, wherein the status indicator is indicative of a progression of a task from a commencement of the task to a completion of the task while the task is being performed;
detect a cognitive state of the user, said user cognitive state being inferred based on performing an assessment of entries in the user's electronic calendar that indicate a potential fatigue; and
modify the status indicator in response to said detecting the cognitive state, said modifying the status indicator comprising applying a mathematical transformation of a level of progress displayed by the status indicator, the mathematical transformation comprising a first derivative of the level of progress displayed by the status indicator or a logarithmic function of the level of progress displayed by the status indicator.

16. The system of claim 15 further comprising one or more sensors or cameras, operatively coupled to the at least one processor, wherein said one or more sensors or cameras are configured for detecting a further cognitive state comprising at least one of fatigue, frustration, anger, happiness, surprise, and a level of distraction.

17. The system of claim 15 wherein said detecting the cognitive state further comprises detecting a cognitive state of a user cohort, said user cohort selected from a group consisting of autism, a child, an elderly individual, an individual suffering from a cognitive impairment due to a neurodegenerative disease, or a cognitive style, wherein to modify, said instructions further configuring said at least one processor to: associate progress bars with different user cohorts.

* * * * *